(12) United States Patent
Lewis

(10) Patent No.: US 11,390,521 B2
(45) Date of Patent: Jul. 19, 2022

(54) METHOD AND SYSTEM FOR CARBON CAPTURE AND RECYCLING

(71) Applicant: Think Tank 42 Pty Ltd, New South Wales (AU)

(72) Inventor: Andrew Lewis, New South Wales (AU)

(73) Assignee: THINK TANK 42 PTY LTD, Heathcote (AU)

( * ) Notice: Subject to any disclaimer, the term of this patent is extended or adjusted under 35 U.S.C. 154(b) by 0 days.

(21) Appl. No.: 16/310,481

(22) PCT Filed: Jun. 16, 2017

(86) PCT No.: PCT/AU2017/050613
§ 371 (c)(1),
(2) Date: Dec. 17, 2018

(87) PCT Pub. No.: WO2017/214687
PCT Pub. Date: Dec. 21, 2017

(65) Prior Publication Data
US 2019/0210872 A1 Jul. 11, 2019

(30) Foreign Application Priority Data
Jun. 18, 2016 (AU) .................................. 2016902386

(51) Int. Cl.
*C01B 3/52* (2006.01)
*C07C 1/12* (2006.01)
(Continued)

(52) U.S. Cl.
CPC ............... *C01B 3/52* (2013.01); *B01D 53/62* (2013.01); *C07C 1/12* (2013.01); *C07C 2/76* (2013.01); *C07C 29/1518* (2013.01); *C10J 3/82* (2013.01); *C10K 3/00* (2013.01); *B01D 2251/404* (2013.01); *B01D 2251/602* (2013.01); *C01B 2203/0283* (2013.01);
(Continued)

(58) Field of Classification Search
None
See application file for complete search history.

(56) References Cited

U.S. PATENT DOCUMENTS 3,488,401 A 1/1970 Ames
3,852,180 A 12/1974 Gregory
(Continued)

FOREIGN PATENT DOCUMENTS

AT 516273 B1 4/2016

OTHER PUBLICATIONS

International Search Report for corresponding international application No. PCT/AU2017/050613, dated Aug. 30, 2017.
(Continued)

*Primary Examiner* — Tam M Nguyen
(74) *Attorney, Agent, or Firm* — Tarolli, Sundheim, Covell & Tummino LLP

(57) ABSTRACT

A method for carbon capture and recycling, the method including the steps of: (i) Capturing $CO_2$ from at least one $CO_2$ containing input; (ii) Producing a $CO_2$ feed stream from the captured $CO_2$; and (iii) Reacting the $CO_2$ feed stream with a $H_2$ feed stream to produce a methane containing output.

10 Claims, 4 Drawing Sheets

(51) Int. Cl.
    *C07C 2/76*     (2006.01)
    *B01D 53/62*     (2006.01)
    *C07C 29/151*     (2006.01)
    *C10J 3/82*     (2006.01)
    *C10K 3/00*     (2006.01)
    *C10L 3/02*     (2006.01)
    *C10L 3/08*     (2006.01)

(52) U.S. Cl.
    CPC ................ *C01B 2203/1241* (2013.01); *C10J 2300/1238* (2013.01); *C10L 3/02* (2013.01); *C10L 3/08* (2013.01); *C10L 2290/02* (2013.01); *C10L 2290/10* (2013.01); *C10L 2290/38* (2013.01); *C10L 2290/543* (2013.01); *Y02C 20/40* (2020.08); *Y02P 20/141* (2015.11)

(56) References Cited

U.S. PATENT DOCUMENTS

| | | | | |
|---|---|---|---|---|
| 5,711,770 | A * | 1/1998 | Malina | C01B 3/042 48/197 R |
| 5,964,908 | A * | 10/1999 | Malina | C01B 3/042 205/628 |
| 10,479,739 | B2 * | 11/2019 | Yates | C25B 1/04 |
| 2002/0055545 | A1 * | 5/2002 | Sheppard | F01K 23/068 518/702 |
| 2004/0115492 | A1 * | 6/2004 | Galloway | C10J 3/02 429/426 |
| 2008/0115495 | A1 * | 5/2008 | Rising | F02C 3/28 60/731 |
| 2009/0165376 | A1 * | 7/2009 | Lau | C10L 3/102 48/73 |
| 2009/0289227 | A1 | 11/2009 | Rising | |
| 2010/0129691 | A1 * | 5/2010 | Dooher | H01M 8/0662 429/425 |
| 2011/0237839 | A1 | 9/2011 | Waldstein | |
| 2012/0134906 | A1 * | 5/2012 | Mastin | B01J 20/3204 423/230 |
| 2013/0154278 | A1 * | 6/2013 | Abughazaleh | C10J 3/56 290/1 R |
| 2013/0172636 | A1 * | 7/2013 | McAlister | C12P 7/04 585/240 |
| 2014/0058149 | A1 | 2/2014 | Negiz et al. | |
| 2014/0080927 | A1 | 3/2014 | Beckett | |
| 2014/0299514 | A1 * | 10/2014 | Horning | C10G 31/06 208/390 |
| 2015/0073188 | A1 * | 3/2015 | Floudas | C07C 5/2767 585/332 |
| 2016/0144314 | A1 * | 5/2016 | Gonnard | E21B 43/40 95/174 |
| 2016/0152528 | A1 | 6/2016 | Petters et al. | |
| 2018/0086985 | A1 * | 3/2018 | von Olshausen | C10G 2/50 |

OTHER PUBLICATIONS

European Extended Search Report for Application No. 17812329.5-1101 dated Dec. 13, 2019.

* cited by examiner

METHOD AND SYSTEM FOR CARBON CAPTURE AND RECYCLING

RELATED APPLICATIONS

The present invention is a U.S. National Stage under 35 USC 371 patent application, claiming priority to Serial No. PCT/AU2017/050613, filed on 16 Jun. 2017; which claims priority of AU 2016902386, filed on 18 Jun. 2016, the entirety of both of which are incorporated herein by reference.

FIELD OF THE INVENTION

The present invention relates to a method and system for carbon capture and recycling, and in particular methods and systems for capturing $CO_2$ and producing methane, acetylene and/or other hydrocarbons.

BACKGROUND

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Climate change is an important issue on the agenda of governments worldwide. It is proposed that climate change is accelerated by human production of "greenhouse gases". Greenhouse gases are those which get trapped in the atmosphere and enhance the "greenhouse effect". In the greenhouse effect, heat is trapped from escaping the earth due to a build up of the greenhouse gases in the atmosphere. Therefore, in seeking to address climate change, several approaches look to reduce green house gas emissions.

Carbon dioxide ($CO_2$) is one green house gas where emissions are targeted. Several approaches have been developed to capture and/or reduce $CO_2$ emissions. One such approach is carbon capture and storage whereby $CO_2$ is captured (e.g. from air, flue gas etc.) and then stored in selected geological rock formations below the earths surface. It will be appreciated that carbon capture and storages can be expensive, and furthermore, no usable products/outputs are produced from the captured $CO_2$, it is simply captured and stored.

The present invention seeks to provide an approach to reducing $CO_2$ emissions that also provides industrially applicable products.

SUMMARY OF THE INVENTION

In one broad form, the present invention provides a method for carbon capture and recycling, the method including the steps of: (i) Capturing $CO_2$ from at least one $CO_2$ containing input; (ii) producing a $CO_2$ feed stream from the captured $CO_2$; and (iii) reacting the $CO_2$ feed stream with a $H_2$ feed stream to produce a methane containing output.

In one form, the method further includes the step of (iv) separating the methane containing output so as to at least provide methane and a first waste output.

In one form, the first waste output is thermally treated to provide $CO_2$ for one of the at least $CO_2$ containing inputs for step (i).

In one form, one of the at least one $CO_2$ containing inputs includes air.

In one form, the $H_2$ feed stream is provided by a water electrolysis process.

In one form, water produced during step (iii) is provided for the water electrolysis process.

In one form, in step (i), $CO_2$ is captured using a Calcium Oxide based capture process.

In one form, the method further includes the step of: (v) processing methane from the methane containing output to produce acetylene containing output.

In one form, the method further includes the step of (vi) separating the acetylene containing output so as to at least provide acetylene and a second waste output.

In one form, the second waste output is thermally treated to provide $CO_2$ for one of the at least one $CO_2$ containing inputs for step (i).

In one form, step (v) includes heating the methane with a thermal plasma reactor.

In one form, the method further includes the step of (vii) processing methane from the methane containing output to produce a hydrocarbon containing output.

In one form, the method further includes the step of (viii) separating the hydrocarbon containing output so as to at least provide one or more preselected hydrocarbon products and a second waste output.

In one form, the second waste output is thermally treated to provide one of the at least one $CO_2$ containing inputs for step (i).

In one form, step (vii) includes heating the methane, and the methane is heated by a thermal plasma reactor configured such that plasma is provided in feed with the methane.

In a further broad form the present invention provides a system for carbon capture and recycling, the system including a $CO_2$ capture apparatus configured to capture $CO_2$ from at least one $CO_2$ containing input; and a first reactor configured to produce a methane containing output from a $CO_2$ feed stream derived from the $CO_2$ capture apparatus and an $H_2$ feed stream.

In one form, the system further includes: a first separator configured to separate the methane containing output so as to at least provide methane and a first waste output.

In one form the system further includes a thermal treatment apparatus configured to treat the first waste output so as to provide $CO_2$ containing input for the $CO_2$ capture apparatus.

In one from, the $CO_2$ capture apparatus is configured to capture $CO_2$ from an air input.

In one form, the system further includes a water electrolysis device for producing the $H_2$ feed stream. In one form the water electrolysis device is configured to receive water for electrolysis produced in the first reactor.

In one form, the $CO_2$ capture apparatus is a Calcium Oxide based capture apparatus.

In one form, the system further includes: a second reactor configured to received methane produced in the first reactor and to produce an acetylene containing output therefrom.

In one form the system further includes: a second separator configured to separate the acetylene containing output so as to at least provide acetylene and a second waste output.

In one from, the second waste output is fed to the thermal treatment apparatus.

In one form, the second reactor is thermal plasma reactor.

In one from, the system further includes a second reactor configured to received methane produced in the first reactor and to produce a hydrocarbon containing output therefrom.

In one form, the system further includes a second separator configured to separate the hydrocarbon containing output so as to at least provide preselected hydrocarbon products and a second waste output.

In one form, the second waste output is fed to the thermal treatment apparatus.

In one form, the second reactor is a thermal plasma reactor configured provide plasma in feed with the methane.

BRIEF DESCRIPTION OF THE DRAWINGS

This invention may be better understood with reference to the illustrations of embodiments of the invention in which.

DETAILED DESCRIPTION

Figure 1:
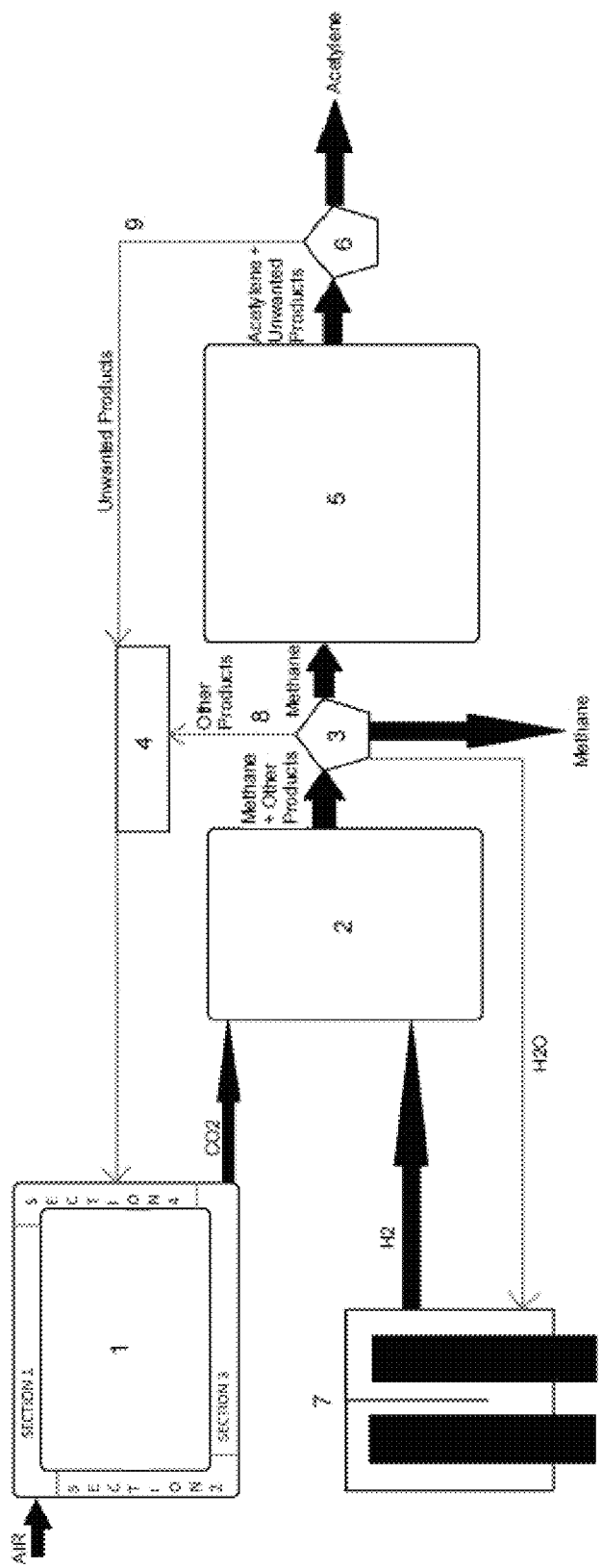
FIG. 1 is an overview layout of one example implementation of the method/system.
Figure 2:
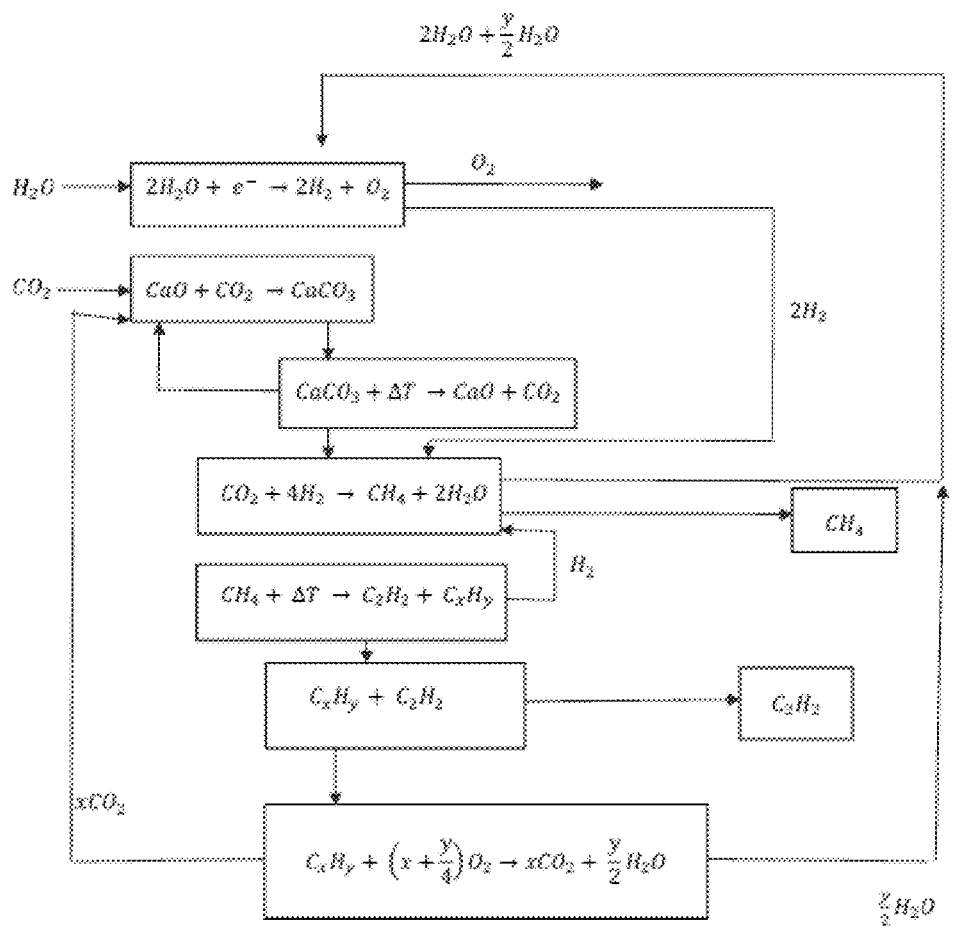
FIG. 2 is an overview of example reactions utilised in one example implementation of the method/system.
Figure 3:
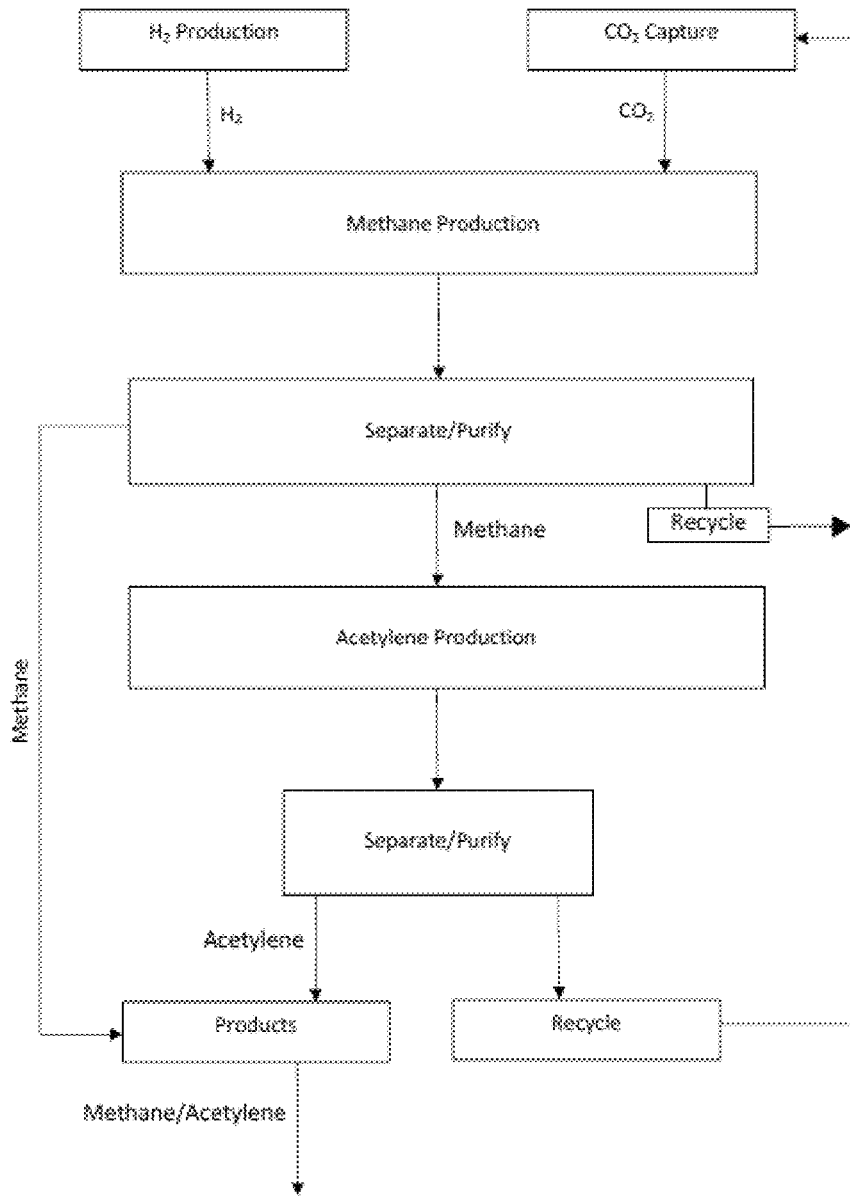
FIG. 3 is a flow chart overview of an example implementation of the method/system.

Embodiments of the present invention provide methods and systems for carbon capture and recycling. Generally, embodiments provide a method/system for producing hydrocarbons from captured carbon, such as, for example, methane or acetylene. The presently described system captures $CO_2$, reducing emissions, and produces industrially applicable output in the form of common precursor materials that may be further processed to form a wide range of materials.

In the methods and systems described, carbon dioxide ($CO_2$) is captured from at least one $CO_2$ containing input/source. It would be appreciated that $CO_2$ may be recovered/captured from a large range of sources, such as, for example, from air, incinerator exhaust streams, or industrial plumes etc. It will also be appreciated that $CO_2$ may be captured using a variety of $CO_2$ capture devices/systems. In the presently described system/method, $CO_2$ is typically captured using a calcium oxide (CaO) based apparatus/system. Calcium Oxide (quicklime) based carbon capture devices/systems have advantages in that the calcium oxide is reusable as a carbon capture agent and permits continuous loop processing as per the below reactions $CaO+CO_2 \rightarrow CaCO_3$ $CaCO_3+\Delta T \rightarrow CaO+CO_2$ As above, CaO reacts with $CO_2$ to form Calcium Carbonate, and subsequent heating of the Calcium Carbonate releases the $CO_2$, providing the CaO for reuse (see Appendix A).

From captured $CO_2$, a $CO_2$ feed stream is produced and fed to a methane producing reactor in combination with a hydrogen ($H_2$) feed stream. A methane containing output is produced by the methane producing reactor. Typically, the methane producing reactor is a conventional batch reactor. It will be appreciated that the $H_2$ feed stream may also be provided from a variety of sources. In one example form, $H_2$ is provided by a water electrolysis process i.e. as per the below reaction $2H_2O+e^- \rightarrow 2H_2+O_2$ The methane containing output form the methane producing reactor typically includes methane, water and other partial products as per the reaction $CO_2+4H_2 \rightarrow CH_4+2H_2O$ The methane containing output is separated to so as to at least provide a substantially pure methane stream and a first waste output stream/recycle stream. It will also be appreciated that separation of the methane containing output may be performed by varying separation devices/methodologies.

The first waste output, is then typically heated by a thermal treatment apparatus (e.g. incinerator) to provide additional $CO_2$ e.g. as per the below reaction $$C_xH_y + \left(x + \frac{y}{4}\right)O_2 \rightarrow xCO_2 + \frac{y}{2}H_2O$$

The additionally produced $CO_2$ (e.g. by the incineration of soot etc.) may then be re-fed into the system via carbon capture to drive more methane production. Additionally, water produced from the production of methane may be re-fed to the water electrolysis process to drive production of additional $H_2$. In some examples, excess water may also be used for cooling and steam generated therefrom used to power turbines etc. Accordingly, it will be appreciated that by products from the reactions at each stage of the process can be re-fed into the system to increase the conversion efficiency, minimise waste, and maximise the methane produced.

Methane produced may further be fed into an acetylene producing reactor so as to produce acetylene containing output e.g. as per the reaction $CH_4+\Delta T \rightarrow C_2H_2$ Typically, the reaction requires heating to high temperature (7000-8000° C.). The acetylene producing reactor is thus typically thermal plasma type reactor, and may, for example be like or similar to the reactors as described in the publication "*Thermal Conversion of Methane to Acetylene Final Report*, J. R. Fincke, R. P. Anderson, T Hyde, R. Wright, R. Bewley, D. C. Haggard, W. D. Swank, Published January 2000, *Idaho National Engineering and Environmental Laboratory*, Idaho Falls, Id. 83415".

As with the methane containing output, the acetylene containing output may be purified/separated to provide a pure acetylene stream and a second waste output stream/recycle stream. The second waste output stream may also be fed back to the thermal treatment apparatus (e.g. incinerator), so as to provide additional $CO_2$ to be re-fed/re-captured by the system.

Alternatively or additionally, produced methane may be processed by a reactor to provide varied/random hydrocarbon containing output. The varied hydrocarbon containing output may then be separated by a separator preconfigured to separate out preselected hydrocarbons. The non-selected output may be provided as a waste output/recycle stream that may then be re-fed to the thermal treatment apparatus, so as to again produce additional $CO_2$ (e.g. by incineration, gasification). The additional $CO_2$ produced being returned for recapture by the carbon capture device/apparatus. The waste output/recycle stream essentially provides a $CO_2$ containing input for the carbon capture device/apparatus. Again the recycle streams from the reactor provide that the methane processing is energy efficient, with waste minimised.

The reactor in this variation is typically of thermal plasma type where plasma is provided in feed with the methane. For example, suitable reactors may be as described in the publication "*Thermal Conversion of Methane to Acetylene Final Report*, J. R. Fincke, R. P. Anderson, T Hyde, R. Wright, R. Bewley, D. C. Haggard, W. D. Swank, Published January 2000, *Idaho National Engineering and Environmental Laboratory*, Idaho Falls, Id. 83415".

One example embodiment of the system and method shall now be described with reference to FIG. 1.

A carbon capture apparatus (1) is provided which is configured to receive one or more $CO_2$ containing inputs/sources. As shown, air may be one of the $CO_2$ containing inputs. It will also be appreciated a range of alternate $CO_2$ containing inputs may be provided such as, for example, waste output streams/recycle streams.

The carbon capture apparatus (1) may take a variety of forms, however, typically, the carbon capture apparatus is a calcium oxide based apparatus. Furthermore, it will be appreciated that calcium oxide may be utilised for carbon capture in a variety of differently configured apparatuses.

The carbon capture apparatus (1) is also configured to produce a $CO_2$ feed gas stream for a methane producing reactor (2).

Typically, the calcium oxide based carbon capture apparatus for use with the present system/method has two preferred configurations. In both configurations, the apparatus typically comprises four chambers with an outlet (e.g. transport tube) for transporting produced $CO_2$ feed to a methane producing reactor (2).

In a first configuration, calcium oxide is mixed with air (containing $CO_2$) in the first chamber via mass transport via air with alternating fans to maximise dispersion and surfaces exposed to the air. $CO_2$ is captured from the air. In the second chamber, a vacuum is formed, and in the third chamber, the now calcium carbonate is baked to 700° C. whilst being stirred (to speed the process). Carbon dioxide is released and flows through outlet to methane producing reactor. A fourth chamber maintains the vacuum between chambers 2, 3, and 4, before the calcium oxide is reused and air rated once more in chamber 1. This is a continuous closed loop.

In a second configuration, calcium oxide is hydrated with water in the first chamber, with air jets on the bottom bubbling air through the mixture while it is pushed along via a spiral configuration. Chamber 2 creates a vacuum and then raises the temperature to 400° C. removing the water, which is fed to chamber 4. In chamber 3, the product is heated to 700° C. while being stirred to release the carbon dioxide to the methane producing reactor. The calcium oxide is then sent to chamber 4, where it is re-hydrated before returning chamber 1 again. Once again, this is a closed loop full of calcium oxide.

Figure 4:
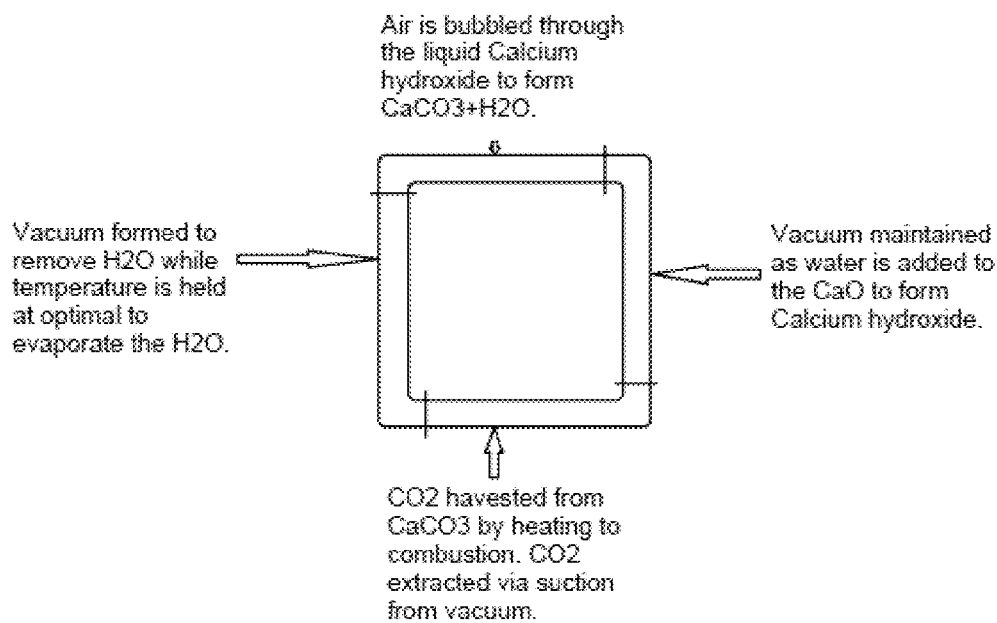
FIG. 4 is an example of $CO_2$ capture apparatus.

Another example configuration of a carbon capture described at FIG. 4.

As shown in FIG. 1, $H_2$ gas is provided to the methane producing reactor to combine with $CO_2$ feed for the production of methane as per the below equation $$CO_2 + 4H_2 \rightarrow CH_4 + 2H_2O$$

It will be appreciated that the reactor (2) provides the appropriate conditions for the production of methane and water from $CO_2$ and $H_2$ (e.g. heating at >600° C. at 1 atmosphere of pressure). Typically, the reactor is heated to about 800° C. Typically the methane producing reactor is a conventional batch rector. It will also be appreciated that the efficiency of this process may be improved by adjusting the reaction conditions such as, for example, by increasing the pressure of the system and the temperature.

The $H_2$ feed stream may come from a variety sources. In the example of FIG. 1, the $H_2$ feed stream is provided by a water electrolysis device (7) which provides $H_2$ as per the following equation $$2H_2O + e^- \rightarrow 2H_2 + O_2$$

As water is produced as a by product in the production of methane, the water can be redirected back to the water electrolysis device (7) for re-use (as shown). In other forms, the water may be used for cooling and/or quenching in subsequent process steps or at other at other parts of the system. Oxygen produced in the electrolysis may be utilised for cleaner combustion in other parts of the system or released to the environment. In some forms, the electrolysis reaction is conducted in a U shaped reactor with a simple barrier with the possible addition of an electrolyte to speed the reaction and lower the energy costs.

A first separator (3) is provided to separate the methane, water and other partial products produced in the methane producing reactor (2). Typically separation is achieved via distillation however it will be appreciated that other methods may be used. Any non-methane and non-water products are separated out into a first waste output and fed to a thermal treatment apparatus (4). The thermal treatment apparatus is typically an incinerator, although, it will be appreciated that it may take other forms such as, for example, a gasifier. Thermal treatment, e.g. incineration, results in additional $CO_2$ product which can then be re-fed to the carbon capture device.

The purified methane from the first separator (3) is directed for further processing to an acetylene producing reactor (5). The acetylene producing reactor (5) provides appropriate reaction conditions to product acetylene form the incoming methane feed stream. Typically, the acetylene is produced via heating as per to the following reaction $$CH_4 + \Delta T \rightarrow C_2H_2$$

In one form, the reactor is a thermal plasma type reactor. In one form, the reactor utilises argon plasma to provide temperatures of about 8000° C. and rapid quenching follows to produce the acetylene. Example reactor/process are described in the publication "*Thermal Conversion of Methane to Acetylene Final Report*, J. R. Fincke, R. P. Anderson, T Hyde, R. Wright, R. Bewley, D. C. Haggard, W. D. Swank, Published January 2000, *Idaho National Engineering and Environmental Laboratory*, Idaho Falls, Id. 83415". Typical yields of acetylene are described in Appendix B. In one example, graphite tubing is utilised in the reactor surrounded by heat exchanges to recapture energy to power the argon plasma jets.

A second separator (6) is used to purify the acetylene containing output, and provide a second waste output/recycle stream (9). Typically separation is achieved via temperature gradient and/or distillation although it will be appreciated a range of appropriate separation methods may be utilised. As with the first waste output stream, the second waste output stream (including soot etc.) is fed to the thermal treatment apparatus (4) for recycling. $CO_2$ produced at the thermal treatment apparatus (e.g. by incineration) is then fed back into the carbon capture apparatus (1). It will be appreciated that in some forms, heat generated from the thermal treatment apparatus (4) may be used to heat the methane and/or acetylene producing reactors. It is noted that the reaction processes in these reactors are exothermic.

Once purified, the acetylene and/or methane produced by the system/process can be readily converted via conventional processes into different polymers, benzo aromatics and other organic compounds for use in a wide variety of industrial applications.

In alternate forms, the acetylene producing reactor may be configured such that the argon plasma (or the like) may be provided in-feed with the methane. This typically results in varied hydrocarbon products being formed rather than mainly acetylene. It will be appreciated that in such examples, the second separator (6) would be configured to filter preselected hydrocarbon products. The remaining non-selected products would be re-fed to the thermal treatment apparatus (e.g. incinerator) for recycling. Again any produced $CO_2$ from combustion/gasification may re-captured for further methane production.

The presently described system/method has significant advantages over conventional carbon capture and storage approaches for reducing $CO_2$ emissions. In particular, there are minimal waste products as the recycle feeds (i.e. waste output streams) push the conversion rate towards 100%.

In addition, once purified, acetylene has many industrial applications and can be further processed and converted, for example, into different polymers, benzo aromatics and other organic compounds. Methane may also be extracted from the system to produce compounds other than those produced by reacting acetylene.

It will be appreciated that power for the various components/reactions may be provided/supplemented by mains electricity, renewable energy sources and waste combustion.

In particular, it will be appreciated that due to the configuration of the system, organic waste material can be directly combusted (e.g. in the thermal treatment apparatus) and filtered to provide the $CO_2$ for the carbon capture. Furthermore, the heat from the combustion also may be supplied to the methane and acetylene producing reactors.

Furthermore, as the methane and acetylene producing reactors are running exothermic processes, once heated, excess energy therefrom may be utilised to further provide electrical energy to the system, while energy recycling may also be used on the coolant for the argon plasma jets. Excess energy may also be harvested by steam turbines to power the argon plasma reactions.

Optional embodiments of the present invention may also be said to broadly consist in the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth.

Although a preferred embodiment has been described in detail, it should be understood that various changes, substitutions, and alterations can be made by one of ordinary skill in the art without departing from the scope of the present invention.

It will be appreciated that various forms of the invention may be used individually or in combination.

APPENDIX A

Calcium oxide is usually made by the thermal decomposition of materials, such as limestone or seashells, that contain calcium carbonate (CaCO3; mineral calcite) in a lime kiln. This is accomplished by heating the material to above 825° C. (1,517° F.), [6] a process called calcination or lime-burning, to liberate a molecule of carbon dioxide (CO2), leaving quicklime.

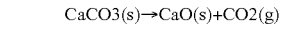

$$CaCO3(s) \rightarrow CaO(s) + CO2(g)$$

The quicklime is not stable and, when cooled, will spontaneously react with $CO_2$ from the air until, after enough time, it will be completely converted back to calcium carbonate unless slaked with water to set as lime plaster or lime mortar.

APPENDIX B

| Reference | Year | Process | Reactor Size | Feedstock | Plasma Gas | Quench Method | Conversion Efficiency | Maximum Acetylene Yield $y_{C2H2}$ | Hydrocarbon Yield other than Acetylene $y_{HC}$ | Normalized Acetylene Yield $y_{C2H2}$ | Soot Yield | Minimum SER kW-hr/$k_g$-$C_2H_2$ |
|---|---|---|---|---|---|---|---|---|---|---|---|---|
| Leutner & Stokes | 1961 | DC plasma jet | 6.8 kW | $CH_4$ | Ar | Wall heat transfer | 92.9% | 80.1 | not analyzed | 86.2 | 5.7% | 72.5 |
| Gladisch | 1962 | Huels DC arc | 8 MW | natural gas | $CH_4$ | Water spray | 70.5% | 51.4% | 45.9% | 72.9% | 2.7% | 12.1 |
| Anderson & Case | 1962 | DC plasma jet | <10 kW | $CH_4$ | $H_2$ | Water spray | >90% | 76% | not analyzed | 88% | not analyzed | 9.16 |
| Holmes | 1969 | DuPont DC arc | 9 MW | $CH_4$ | $H_2$ | not reported | not reported | 70% | not reported | | not reported | 8.8 |
| Ibberson & Sen | 1976 | DC plasma jet | <10 kW | $CH_4$ | Ar | Wall heat transfer | >90% | 82% | not reported | 91% | not analyzed | 9.0 |
| Plotczyk | 1983 | DC plasma jet | 10-40 kW | $CH_4$ | $H_2$ | Wall heat transfer | 95% | 80% | not analyzed | 84% | not analyzed | 15.5 |
| Kovener | 1983 | RF plasma | 4 kW | $CH_4$ & natural gas | He | Wall heat transfer | not reported | not reported | not reported | — | not reported | 88 |
| Plotczyk | 1985 | DC plasma jet | 4-16 kW | $CH_4$ | Ar | Wall heat transfer | >90% | 86% | not reported | 95% | not reported | 23.9 |

The invention claimed is:

1. A method for recycling $CO_2$ from $CO_2$ containing inputs to produce hydrocarbon products, the method including the steps of:
   (i) capturing $CO_2$ from at least one $CO_2$ containing input, wherein one of the at least one $CO_2$ containing input includes air;
   (ii) producing a $CO_2$ feed stream from the captured $CO_2$;
   (iii) reacting the $CO_2$ feed stream with a $H_2$ feed stream to produce a methane containing output;

(iv) separating the methane containing output so as to at least provide methane and a first waste output, wherein the first waste output is incinerated or gasified to provide one of the at least one $CO_2$ containing inputs for step (i);

(v) processing methane from the methane containing output to produce an acetylene containing output; and (vi) separating the acetylene containing output so as to at least provide acetylene and a second waste output.

2. A method as claimed in claim 1, wherein one of the at least one $CO_2$ containing inputs is derived from incinerator exhaust streams or industrial plumes.

3. A method as claimed in claim 1, wherein the $H_2$ feed stream is provided by a water electrolysis process.

4. A method as claim in claim 3, wherein water produced during step (iii) is provided for the water electrolysis process.

5. A method as claimed in claim 1 wherein, in step (i), $CO_2$ is captured using a Calcium Oxide sorbent.

6. A method as claimed in claim 1, wherein the second waste output is incinerated or gasified to provide one of the at least one $CO_2$ containing inputs for step (i).

7. A method as claimed in claim 6, wherein step (v) includes heating the methane with a thermal plasma reactor.

8. A method as claimed in claim 1, further including the step of (v) heating methane from the methane containing output with a thermal plasma reactor to produce a hydrocarbon containing output, wherein the thermal plasma reactor is configured such that plasma is provided in feed with the methane.

9. A method a claimed in claim 8, further including the step of (vi) separating the hydrocarbon containing output so as to at least provide one or more preselected hydrocarbon products and a second waste output.

10. A method as claimed in claim 9, wherein the second waste output is incinerated or gasified to provide one of the at least one $CO_2$ containing inputs for step (i).

\* \* \* \* \*